United States Patent [19]

Kim et al.

[11] Patent Number: 5,487,983
[45] Date of Patent: Jan. 30, 1996

[54] EXPRESSION SYSTEMS FOR MAKING SINGLE-CHAIN MONELLIN ANALOGS

[75] Inventors: Sung-Hou Kim; Joong M. Cho, both of Moraga, Calif.

[73] Assignees: The Regents of the University of California, Berkeley; Lucky, Ltd., Emeryville, both of Calif.

[21] Appl. No.: 146,326

[22] Filed: Nov. 2, 1993

Related U.S. Application Data

[60] Division of Ser. No. 502,257, Mar. 30, 1990, Pat. No. 5,264,558, which is a continuation-in-part of Ser. No. 465,585, Jan. 18, 1990, abandoned, which is a continuation of Ser. No. 117,124, Nov. 4, 1987, abandoned, and a continuation-in-part of Ser. No. 64,341, Jun. 19, 1987, abandoned, and a continuation-in-part of Ser. No. 64,343, Jun. 19, 1987, abandoned.

[51] Int. Cl.$^6$ .............................. C12P 21/06; C12N 5/06; C12N 15/03; C07H 21/04
[52] U.S. Cl. ................. 435/69.1; 435/240.2; 435/240.4; 435/253.2; 435/320.1; 536/23.6
[58] Field of Search .................. 435/320.1, 69.1, 435/252.3, 240.2, 240.4; 536/23.6

[56] References Cited

U.S. PATENT DOCUMENTS 5,234,834  8/1993  Fischer et al. ....................... 435/320.1

OTHER PUBLICATIONS

Ogata, C. et al. Nature (1987) 328: 739–742.
*Protein Stability & Stabilization Through Protein Engineering*, Nosoh et al., 1991, Ellis Horwood, pub., N.Y. p. 62.

*Primary Examiner*—W. Gary Jones
*Assistant Examiner*—Lisa Arthur
*Attorney, Agent, or Firm*—Morrison & Foerster

[57] ABSTRACT

Single-chain analogs of the naturally occurring two-chain peptide monellin retain the sweetening properties of the natural protein and are stable under conditions which would otherwise destabilize the native peptide. A covalent linkage joins peptides corresponding to portions of the A and B chains of the naturally occurring protein.

12 Claims, 2 Drawing Sheets

AMINO ACID SEQUENCE OF NATURAL MONELLIN

A-Chain

```
  1
 *PHE ARG GLU ILE LYS GLY TYR GLU TYR GLN
  LEU TYR VAL TYR ALA SER ASP LYS LEU PHE
  ARG ALA ASP ILE SER GLU ASP TYR LYS THR
  ARG GLY ARG LYS LEU LEU ARG PHE ASN GLY
  PRO VAL PRO PRO PRO
                   45
```

FIG. 1

B-Chain

```
  1
  GLY GLU TRP GLU ILE ILE ASP ILE GLY PRO
  PHE THR GLN ASN LEU GLY LYS PHE ALA VAL
  ASP GLU GLU ASN LYS ILE GLY GLN TYR GLY
  ARG LEU THR PHE ASN LYS VAL ILE ARG PRO
  CYS MET LYS LYS THR ILE TYR GLU ASN GLU
                                       50
```

* PHE presents only in 10 % of natural monellin

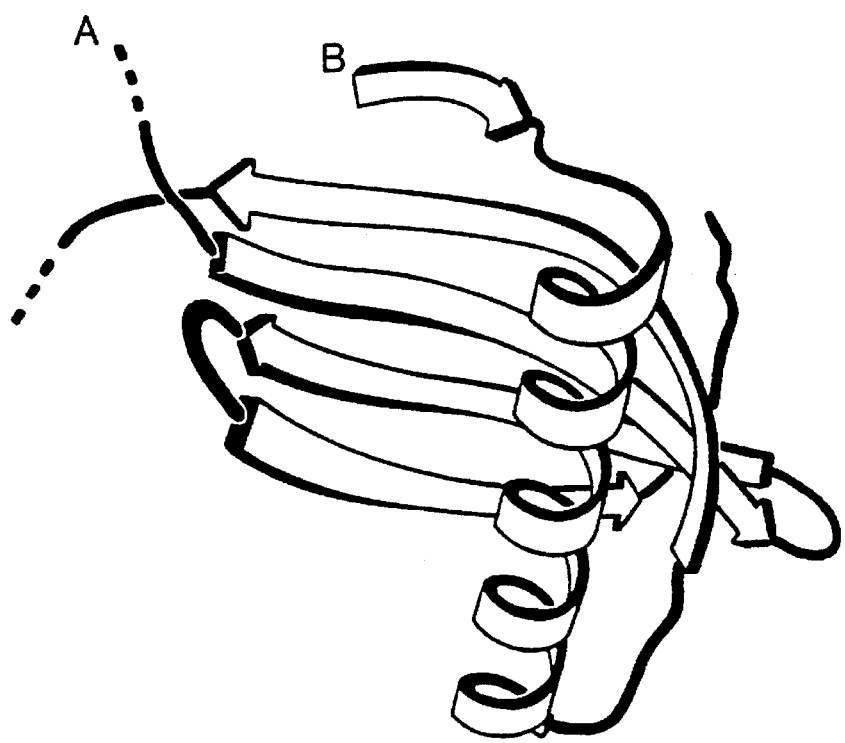

FIG. 2

EXPRESSION SYSTEMS FOR MAKING SINGLE-CHAIN MONELLIN ANALOGS

The Government has rights in this invention pursuant to NIH Grant No. NS-15174 awarded by the Department of Health and Human Services. This application is a divisional of application U.S. Ser. No. 07/502,257 filed Mar. 30, 1990, now issued as U.S. Pat. No. 5,264,558, which is a continuation-in-part of U.S. Ser. No. 07/465,585 filed Jan. 18, 1990 and now abandoned which is a file wrapper continuation of U.S. Ser. No. 07/117,124 filed Nov. 4, 1987, now abandoned, and is also a continuation-in-part of U.S. Ser. No. 07/064,341 filed Jun. 19, 1987 and now abandoned as well as a continuation-in-part of U.S. Ser. No. 07/064,343 filed Jun. 19, 1987 and now abandoned.

TECHNICAL FIELD

The invention relates to using proteins as substitutes for sugar in sweetening foods and beverages. In particular, it concerns single chain proteinaceous compounds which are much sweeter than sucrose, and which retain their sweetening capacity although subjected to brief heating conditions.

BACKGROUND OF THE INVENTION

It is well known that certain proteinaceous compounds have the ability to substitute in a highly effective manner for sugar in giving foods and beverages a sweet taste. The simplest of these examples is aspartame, which is a dipeptide derivative and currently on the market. However, two much more complex proteins, monellin and thaumatin have been isolated from plant sources. Thaumatin is isolated from *Thaumatococcus daniellii*, a West African plant having triangular shaped fruit at ground level. The natural protein product, thaumatin, has an average sweetness of 2500 times that of sucrose and has been marketed under the trademark Talin. The three-dimensional structure of this protein has been studied and the results published by De Vos, A. M., et al., *Proc Natl Acad Sci* USA (1985) 82:1406–1409.

The other protein is isolated from "Serendipity Berries" of the West African Plant *Dioscoreophyllum comminisii*. The amino acid sequence of monellin is known, and the three-dimensional structure of this protein has been determined by Ogata, C., et al., *Nature* (1987) 328:739–742. Monellin has been characterized by Morris et al., *J Biol Chem* (1973) 248:534–539, and by others; Cagan, *Science* (1973) 181:32–35; Bohak and Li, *Biochim Biophys Acta* (1976) 427:153–170; Hudson and Beeman, *Biochem Biophys Res Comm* (1976) 71:212–220; Van der Wel and Loeve, *FEBS Lett* (1973) 29:181–183; Frank and Zuber Hoppe-Seyler's *Z Physiol Chem* (1976) 357:585–592; Morris and Cagan, *Biochim Biophys Acta* (1972) 261:114–122. U.S. Pat. No. 3,998,798 describes the preparation of natural monellin.

The known amino acid sequence of the A and B chains of natural monellin is shown in FIG. 1. It is a two chain peptide, one "A" chain containing 45, and the other "B" chain, 50 amino acid residues. The three-dimensional conformation of the protein, shown in FIG. 2, is evidently essential for its activity because when native monellin is heated to 90° C. at neutral pH or to 50° C. at acidic pH and then cooled, the sweetness is destroyed.

The three-dimensional conformation of the protein as recently determined (supra) is shown in FIG. 2. A B chain containing 50 amino acids is intimately associated with the A chain of 45 amino acids in such a way that there are many interchain interactions. Heating of the protein, evidently dissociates the chains in such a way that they are incapable of reforming into the appropriate conformation.

It has now been found that the conformation of this proteinaceous compound can be maintained by synthesizing portions of the B and A components on a single molecule. This constraint results in resistance to denaturation and ease of renaturation and of maintaining the three-dimensional conformation. Furthermore, the proteinaceous compound can be made by synthetic or recombinant techniques, and the uncertainties and expense of extraction from natural sources are thereby obviated.

DISCLOSURE OF THE INVENTION

The invention provides single chain forms of the sweet proteinaceous substance, monellin, which are capable of maintaining their three-dimensional conformation under conditions which would ordinarily denature the native protein. These forms retain their sweet taste, which is substantially more intense than that of sucrose, even after heating to 100° C. at acidic pH. Thus, the substance remains useful for sweetening of foods and beverages including carbonated beverages exposed to temperatures above ambient.

In one aspect the invention is directed to a single chain proteinaceous compound having a sweetness property at least 50, preferably 100, and most preferably 1000 times that of sucrose on a weight basis. The compound has the formula B-C-A wherein B is substantially equivalent to the residues 1–46 of the B chain (or Subunit II) portion of native monellin and is linked through the C-terminus to C. C is a covalent bond or a covalent linker which is, in turn, linked to the N-terminus of a peptide substantially equivalent to residues 6–45 of the A chain (Subunit I) of native monellin. The covalent linker, C, must be of an approximate length the equivalent of up to a 10 alpha-amino acid peptide, of sufficient hydrophilicity to reside on the outer side of the molecule, and must be physiologically acceptable. If C is a covalent bond or is a covalent linker which is itself a peptide, the substance will be a single chain protein which can be prepared using automated synthetic methods or can be prepared from a synthetic or other cloned gene using recombinant techniques, or by other methods known in the art.

As recombinant methods may also be used, the invention, in another aspect, includes DNA sequences encoding the protein, expression vectors containing these sequences, microorganisms or other host cells transformed with these vectors, and methods to produce the protein using these materials. The invention also includes useful intermediates in the synthesis of the compounds of the invention.

BRIEF DESCRIPTION OF THE DRAWINGS

FIG. 1 shows the amino acid sequence of the A and B chains of the native protein.

FIG. 2 is a representation of the three-dimensional conformation of the native protein.

MODES OF CARRYING OUT THE INVENTION

Figure 3:
FIG. 3 shows the amino acid sequence of a single chain protein of the invention, and the nucleotide sequence of a synthetic gene useful in synthesizing said single chain protein.

The proteinaceous compounds of the invention, useful as sweeteners, consist essentially of a peptide portion substantially equivalent to the sequence of residues 1–45 of the B chain which corresponds to Subunit II of native monellin linked through the C-terminus directly by a covalent bond by a covalent linker to the N-terminus of a peptide substantially equivalent to the sequence of residues 6–45 of A chain, corresponding to Subunit I, of native monellin. By "substantially equivalent" is meant a peptide which, in the context of the compounds of the invention, results in a substance having a sweetening power at least 50 times that of sucrose, and which has at least 50% homology with the peptide represented by residues 1–46 of the B chain or to the peptide represented by residues 6–45 of the A chain, preferably 80% homology. At least 90% homology is preferred, especially including conservative substitutions.

Homology is calculated by standard methods which involve aligning two sequences to be compared so that maximum matching occurs, and calculating the percentage of matches. Thus, in a particularly preferred embodiment, the substances of the invention comprise a peptide having the amino acid sequence of residues 1–46 of the native monellin B chain linked (through the linker) to a peptide having the primary structure represented by residues 6–45 of the native monellin A chain. Substantially equivalent substances to these include those wherein one or more of the residues of the native sequence is deleted, substituted for, or inserted by a different amino acid or acids.

Preferred substitutions are those which are conservative, i.e., wherein a residue is replaced by another of the same general type. As is well understood, naturally occurring amino acids can be subclassified as acidic, basic, neutral and polar, or neutral and nonpolar. Furthermore, three of the encoded amino acids are aromatic. It is generally preferred that peptides differing from the native sequence contain substitutions which are from the same group as that of the amino acid replaced. Thus, in general, the basic amino acids Lys, Arg, and His are interchangeable; the acidic amino acids aspartic and glutamic are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable. While proline is a nonpolar neutral amino acid, it represents difficulties because of its effects on conformation, and substitutions by or for proline are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by amino acids from different classes may also be useful to modify sweet taste responses.

It should further be noted that substitutions by amino acids which are not encoded by the gene may also be made. Alternative residues include, for example, the omega amino acids of the formula $H_2N(CH_2)_nCOOH$ wherein n is 2–6. These are neutral, nonpolar amino acids, as are sarcosine (Sar), t-butyl alanine (t-BuA), t-butyl glycine (t-BuG), N-methyl Ile (N-MeIle), and norleucine (Nle). Phenyl glycine, for example, can be substituted for Trp, Tyr or Phe an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be retained if one or more of these is substituted by hydroxyproline (Hyp).

In general, whatever substitutions are made are such that the sweetness of the intact proteinaceous molecule is retained and ancillary properties, such as non-toxicity are not substantially disturbed.

In addition, one or more of the peptide linkages in the B or A peptide-corresponding portions of the substances of the invention may be replaced with other types of linkages which retain the same general properties such as —$CH_2NH$—, —$CH_2S$—, —$CH_2CH_2$—, —$CH=CH$—, —$COCH_2$—, —$CH(OH)CH_2$—, and —$CH_2SO$— by methods known in the art. See, for example, Spatola, A. F. *Vega Data* (1983), 1(3), "Peptide Backbone Modifications"; Spatola, A. F., in "Chemistry and Biochemistry of Amino Acids, Peptides and Proteins", B. Weinstein, ed., Marcel Dekker, New York, p. 273 (1983); Morley, J. S., *Trans Pharm Sci* (1980), pp. 463–468. These substitutions may be made so long as the resulting "protein" is physiologically acceptable.

It should be further noted that if the protein embodiments of the invention are produced recombinantly as intracellular proteins, an N-terminal methionine residue may be retained in the finished product. Cleavage of this N-terminal methionine to liberate the native sequence may or may not be complete.

The covalent linkage between the portions corresponding to the monellin subunit sequences is, generally, of a length equivalent to that generated by a peptide of up to 10 amino acid residues, preferably 6–8 amino acid residues, and must be physiologically acceptable. By "physiologically acceptable" is meant nontoxic and free of undesirable side effects. The bridging portion, C, can be either simply a covalent bond or can contain additional atoms and is then referred to as a "bridge" or covalent linker. This bridge should have a hydrophilicity and length which permits the covalent linker to reside on the external portion of the molecule and not to distort the native conformation. One preferred covalent peptide linking sequence is
Tyr-Glu-Asn-Glu-Arg-Glu-Ile-Lys,
which corresponds to the amino acids in positions 47–50 of the monellin B chain (Subunit II) followed by the amino acids in positions 2–5 of the A chain (Subunit I). The amino acid Phe, in position 1 of the A chain, is absent from the major species of native protein.

If the bridge is composed of amino acids, it will provide for a polar bridge wherein at least 50%, preferably at least about 75% of these amino acids are polar. Also preferably, at least about 25% and more preferably about 50% will be amino acids naturally occurring at the termini of the subunits.

A particularly preferred group of covalent linkers represented by C comprises a peptide sequence containing 3–10, preferably 6–8, amino acid residues of the formula
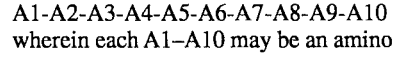
wherein each A1–A10 may be an amino acid residue or may be absent, but at least three of A1–A10 must be amino acid residues. In a particularly preferred group of embodiments, A9 and A10 are absent, A2, A4 and A6 are acidic amino acids; A5 and A8 are basic amino acids, A3 is a polar/neutral amino acid, and A1 and A7 are nonpolar amino acids.

In another set of preferred embodiments, A9 and A10 are absent and
A1 is Ala, Asp, Glu, Lys, Arg or Tyr;
A2 is Tyr, Ala, Asp, Glu, Asn, Gln, Arg, Thr, or Ser;
A3 is Asn, Gln, Ser, Thr, Asp, Gly, Arg or Tyr;
A4 is Phe, Trp, Tyr, Ser, Thr, Asp, Lys or Arg;
A5 is Asp, Glu, Lys, Arg, Leu or Thr;
A6 is Asp, Glu, Val, Ile, Leu, Lys or Arg;
A7 is Gly, Ala, Val, I le, Leu, Lys or Arg; and A8 is Lys or Arg;
wherein at least 75% of these amino acids are polar and wherein one or more of A1–A8 may be absent. In another set of preferred embodiments, A9 and A10 are absent and the remaining amino acids are according to:

A1 is Tyr or Glu;
A2 is Asp, Glu, Tyr or Lys;
A3 is Asn, Thr, Ala or Tyr;
A4 is Arg, Ser, Lys or Glu;
A5 is Glu, Asp or Thr;
A6 is Lys, Asp or Arg;
A7 is Gly, Ile or Leu; and
A8 is Lys or Arg;

wherein at least 75% of the residues are polar and 1 or more of A1–A8 may be absent.

In a particularly preferred set of embodiments, A9 and A10 are absent, A1 is Tyr or Phe, A2 is Glu or Asp, A3 is Asn or Gln, A4 is Glu or Asp, A5 is Arg, His, or Lys, A6 is Glu or Asp, A7 is Ile, Val, or Leu, and A8 is Arg, Lys, or His.

Particularly preferred are the following bridges:
Tyr-Glu-Asn-Arg-Glu-Asp-Ile-Lys;
Tyr-Lys-Thr-Arg-Glu-Asp-Ile-Lys;
Tyr-Glu-Arg-Glu-Ile-Lys;
Tyr-Glu-Asn-Ile-Lys;
Tyr-Glu-Ile-Lys;
Tyr-Tyr-Ala-Ser-Asp-Lys-Leu-Lys;
Tyr-Ala-Ser-Asp-Lys;
Tyr-Ala-Ser-Asp-Lys-Leu;
Tyr-Ser-Asp-Lys;
Glu-Asp-Tyr-Lys-Thr-Arg-Gly-Arg; and
Glu-Asp-Tyr-Thr-Arg.

Usually there will be at least one Tyr, Glu, Asp, Lys or Arg present in the chain, and more usually at least one of Glu, Asp, Lys or Arg. Preferred amino acids for the bridge are Tyr, Ile, Ser, Thr, Asp, Glu, Lys, Arg, Asn and Gln where more than 50% of the amino acids of the bridge will be selected from this group.

Unless otherwise noted, the amino acid residues whether encoded by the gene or as nonencoded analogs, are in the L-configuration. However, two of such residues, preferably one, may be substituted by the D-isomer.

Alternative linkers include any covalent linking moiety which is of the appropriate length as described above, appropriate hydrophilicity, and physiological acceptability. For example, polyethylene glycol oligomers of the formula $HO(CX_2CX_2O)_nH$ wherein each X is independently H or a saturated or unsaturated hydrocarbyl of 1–4C and wherein n is 1–10, preferably 3–8, can also be used. Oxidation of one of the terminal hydroxyl groups provides a carboxyl for formation of the amide to the N-terminus of the A chain; linkage to the B chain is through an ester linkage with the remaining hydroxyl of the polyethylene glycol. A variety of covalent linkers of the correct functionality, hydrophilicity and length can be provided and used to effect covalent linkage of the C-terminus of the B chain with the N-terminus of the A chain. A variety of such covalent linkers is available commercially, for example, from Pierce Chemical Company, Rockford, Ill.

The B and A peptides of the invention compounds, and the C linking portion, if it, too, is a peptide, can be synthesized using standard automated peptide synthesis techniques, either manually or on automated synthesizers such as those supplied by Applied Biosystems (Foster City, Calif.), or Biosearch (San Rafael, CA). Resins derivatized to the C-terminal amino acid in protected form are commercially available. Thus, for synthesis of the A chain portion, resins derivatized with proline are preferred; for the B portion, in a preferred embodiment, those derivatized to Ile. The subsequent amino acids are added using standard techniques to synthesize peptides of the required length. The A and B chains can each be synthesized in toto or as fragments which are then ligated, and subsequently linked with the covalent linker to obtain the substances of the invention.

If prepared using recombinant techniques, a DNA sequence encoding the desired peptide portion, in some cases the full-length peptide representing the proteinaceous sweetener of the invention, is synthesized using standard automated techniques, or the coding sequences or portions thereof are retrieved from cDNA or genomic libraries. This DNA is ligated into suitable expression vectors and these vectors are transformed into appropriate hosts. A variety of expression vector/host cell systems can be used, including both procaryotic and eucaryotic culture systems.

Procaryotes most frequently are represented by various strains of E. coli. However, other microbial strains may also be used, such as bacilli, for example *Bacillus subtilis*, various species of *Pseudomonas*, or other bacterial strains. In such procaryotic systems, plasmid vectors which contain replication origins, and control sequences derived from a species compatible with the host are used. For example, E. coli is typically transformed using derivatives of pBR322, a plasmid derived from an E. coli species by Bolivar et al., *Gene* (1977) 2:95. Commonly used procaryotic control sequences, which are defined herein to include promoters for transcription initiation, optionally with an operator, along with ribosome binding site sequences, include such commonly used promoters as the beta-lactamase (penicillinase), lactose (lac) promoter systems (Chang et al., *Nature* (1977) 198:1056), the tryptophan (trp) promoter system (Goeddel et al., *Nucleic Acids Res* (1980) 8:4057), and the lambda-derived $P_L$ promoter and N-gene ribosome binding site (Shimatake et al., *Nature* (1981) 292:128). However, any available promoter system compatible with procaryotes can be used.

The expression systems useful in the eucaryotic systems of the invention comprise promoters derived from appropriate eucaryotic genes. A class of promoters useful in yeast, for example, include promoters for synthesis of glycolytic enzymes, including alcohol dehydrogenase-1 promoter, glyceraldehyde-3-phosphate dehydrogenase promoter (Holland & Holland, *J Biol Chem* (1980) 25:2596), alpha-factor promoter (Bitter et al., *Proc Natl Acad Sci* (1984) 81:5330), the gal promoter (Johnston & Davis, *Mol Cell Biol* (1984) 4:1440) those for 3-phosphoglycerate kinase (Hitzeman et al., *J Biol Chem* (1980) 256:2073). Other promoters include those from the enolase gene (Holland, M. J., et al., *J Biol Chem* (1981) 256:1385) or the Leu2 gene obtained from YEp13 (Broach, J., et al., *Gene* (1978) 8:121).

Suitable mammalian promoters include the early and late promoters from SV40 (Fiers et al., *Nature* (1978) 273:113) or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter is appropriate (Depicker, A., et al., *J Mol Appl Gen* (1982) 1:561).

The expression systems are included on replication vectors or are caused to integrate into the chromosome of a recombinant host. For systems wherein the vectors include a replication system, these may be low or high copy number, usually having copy numbers of fewer than about 1000, although in certain situations, runaway vectors may be employed. Whether provided on a vector intended for integration or in a replication system, the sequence encoding the proteinaceous sweetener of the invention may be ligated in tandem with an amplifying gene such as dihydrofolate reductase, metallothioneins, thymidine kinase or the like. In procaryotic systems, both the amplifying gene and the sweetener gene may be under the regulation of the same transcriptional and translational regulatory regions.

Usually, the vector will include a marker which allows for selection of host cells containing the expression system; the nature of these markers depends on the host and is understood in the art. In addition to required regulators such as promoters, additional sequences such as enhancers may also be employed to enhance the level of transcription. If the sweetener is to be secreted, an upstream sequence encoding signal peptides such as those described in U.S. Pat. Nos. 4,336,336; 4,338,397; and 4,546,082 may be employed. The signal sequence is enzymatically cleaved as the protein product is secreted.

Depending on the host cell used, transformation is done using standard techniques appropriate to such cells. The calcium treatment employing calcium chloride, as described by Cohen, S. N., *Proc Natl Acad Sci USA* (1972) 69:2110, or the RbCl method described in Maniatis et al., *Molecular Cloning: A Laboratory Manual* (1982) Cold Spring Harbor Press, p. 254 is used for procaryotes or other cells which contain substantial cell wall barriers. Infection with *Agrobacterium tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:2:546 is preferred. Transformations into yeast are carried out, for example, according to the method of Van Solingen, P., et al., *J Bacter* (1977) 130:946; and Hsiao, C. L., et al., *Proc Natl Acad Sci USA* (1979) 76:3829.

In general, after construction of a suitable expression system, the system is transfected into the appropriate host and successful transformants are selected by markers contained on the expression vectors. Successfully transformed colonies are then cultured in order to produce the desired protein. It is sometimes preferred that a promoter which can be controlled by regulating conditions in the environment be used so that the cells can be grown under conditions where the gene encoding the desired protein of the invention is not expressed, and then production of the protein induced by appropriate manipulation of conditions. For example, if the trp promoter is used in E. coli, the cells are grown in the presence of tryptophan and expression is then induced by diminution of tryptophan concentration or by addition of a tryptophan analog such as indolylacetic acid. If the gene is under control of the PL promoter, the cells are grown at relatively low temperature, such as at about 35° C., to a suitable cell density, and the temperature is then elevated to activate this promoter. If produced in bacterial hosts as a mature intracellular protein, the N-terminal methionine may or may not be cleaved. In mammalian systems, for example, the use of the metallothionein promoter permits induction by addition of heavy metals or glucocorticoids. This protocol is preferred to prevent premature accumulation of the protein which may be harmful to the growth of the cell.

The protein may be produced intracellularly, or in secreted form by construction of vectors wherein the peptide is preceded by a signal peptide workable in the appropriate host.

The protein is recovered from the medium or from the cells using suitable techniques generally known in the art, and purified by, for example, ion exchange chromatography, ammonium sulfate precipitation, gel permeation chromatography, and so forth.

Rather than providing the sweetener as an independent product, the expression system described above can be prepared for use in plants to result in naturally sweetened plant products. In this embodiment, the control regions responsible for the expression of the coding sequences which are functional in plants are employed. Transcription initiation regions, for example, include the various opine initiation regions, such as octopine, mannopine, nopaline and the like. Plant viral promoters can also be used, such as the cauliflower mosaic virus 35S promoter. In addition, plant promoters such as ribulose-1,3-diphosphate carboxylase, fruit-specific promoters, heat shock promoters, seed-specific promoters, etc. can also be used. Plants transformed with this expression system offer production of naturally sweetened fruits and vegetables.

Preparation of Antibodies

The sweetening compounds of the invention, however prepared, and whatever the nature of the linkage represented by C, may also be used to generate antibodies immunospecific for those invention compounds which are useful in purification of the compounds from synthetic or bioculture media. These antibodies may be prepared using standard immunization techniques by mixing the compound with suitable excipients and injecting the preparations into vertebrate hosts, typically rabbits or other mammalian hosts. The antisera or purified antibodies can then be conjugated to solid supports to provide immunoaffinity columns for purification of the desired materials.

Applications

The proteinaceous substances of the invention of the formula B-C-A, however prepared, can be used as sweetening elements in foods and beverages. Since the substances of the invention have a sweetening capacity at least 100 times that of sucrose, small quantities can be used to supplement the flavoring of juices, carbonated beverages, and other soft drinks. The sweeteners can also be used as sugar substitutes in hot beverages such as coffee and tea since the conformation is maintained at elevated temperatures. These materials can also be used to sweeten animal feeds, and can be used in a variety of products such as chewing gum, toothpaste, mouthwash, dental hygiene products, and pharmaceuticals. In addition, the sweetener can be used in foodstuffs such as meat products, instant soups, yogurt, desserts, cereals, and so forth.

For those embodiments of the invention compounds which are encoded by DNA sequences, the materials may be produced in situ by transfected microorganisms, eucaryotic cell lines, or plants. For example, expression systems containing the gene encoding the desired substance can be transfected into the culture organisms used in production of yogurt, wine, beer and the like and the sweetener produced along with the production of the desired product. In addition, expression systems operable in plants including the gene encoding the invention compounds may be used to transfect explants or plant protoplasts, and these then regenerated into intact plants which are then genetically capable of production of sweeter forms of fruit or vegetable products.

When used as a sweetener product, the compounds of the invention will be typically extended by addition of a liquid or powders wherein the compound of the invention constitutes about 0.1–99% by weight of the composition. Suitable extenders include, for example, inert powders such as cellulose and may include additional helpful ingredients such as antioxidants, preservatives, protease inhibitors, and so forth.

Examples

The following examples are intended to illustrate the invention but not to limit its scope.

Example 1

Preparation of the Synthetic Gene

The protein of the amino acid sequence shown in FIG. 3 is encoded by a DNA sequence as there shown. As shown in FIG. 3, nucleotides 1–141 encode residues 1–45 of the native B chain preceded by a met encoding ATG start codon, nucleotides 142–165 encode the linking "C" portion of 8 amino acids, and nucleotides 166–285 encode residues 6–45 of the native A protein.

This synthetic gene was prepared from the following oligomers, synthesized using Applied Biosystems 380B DNA Synthesizer.

water-bath and cooled slowly to room temperature overnight. To the mixture was added 7 ul of 10 mMATP, 40 units of T4 DNA ligase (New England Biolab Inc.) and 2 ul of water.

The reaction mixture was kept at room temperature for 10 minutes, extracted by phenol/ chloroform, precipitated, dried and redissolved in 85 ul water. The ligated oligomer mixture was treated with restriction endonuclease NdeI and SalI (New England Biolabs, Inc.), and the 290 base pair fragment was isolated by electrophoresis with a 7% polyacrylamide gel, the band electroeluted and purified using the Elutip-D column (S&S Co.).

M13mp19RF was used for cloning the synthetic monellin gene. M13mp19RF was cut with XbaI/SalI (New England Biolabs, Inc.), and the large fragment was isolated and purified. A synthetic XbaI/NdeI adaptor,

| XbaI | | NdeI |
|---|---|---|
| 5' - CTAGAAACTGCAATGTTGAATAAACGCTGATTTTCGATCA - 3' | | (40 mer) |
| 3' - TTTGACGTTACAACTTATTTGCGACTAAAAGCTAGTAT - 5' | | (38 mer) | was purified, and the NdeI/SalI digested, annealed synthetic monellin DNA fragment prepared above was combined with XbaI/SalI-treated M13mp19RF and XbaI/NdeI adaptor in 10 ul of 20 mM Tris-HCl, pH 7.5, 10 mM $MgCl_2$, 10 mM DTT, 200 units T4 DNA ligase (New England Biolabs, Inc.)

5' → 3'
| | | |
|---|---|---|
| U1: | TATGGGAGAATGGGAAATTATCGATATTGGACCATTCACTCAAAAC | (46 mer) |
| U2: | TTGGGTAAGTTCGCTGTTGACGAAGAAAACAAGATTGGTCAATAT | (45 mer) |
| U3: | GGTAGATTGACTTTCAACAAGGTTATTAGACCATGTATGAAGAAG | (45 mer) |
| U4: | ACTATTTACGAAAACGAAAGAGAAATTAAGGGGTACGAATACCAA | (45 mer) |
| U5: | TTGTATGTTTACGCTTCTGACAAGCTTTTCAGAGCTGACATTTCT | (45 mer) |
| U6: | GAAGACTACAAGACCCGCGGTAGAAAGTTGTTGAGATTCAACGGT | (45 mer) |
| U7: | CCAGTTCCACCACCATAATAG | (21 mer) |
| L1: | CGATAATTTCCCATTCTCCCA | (21 mer) |
| L2: | CGTCAACAGCGAACTTACCCAAGTTTTGAGTGAATGGTCCAATAT | (45 mer) |
| L3: | CCTTGTTGAAAGTCAATCTACCATATTGACCAATCTTGTTTTCTT | (45 mer) |
| L4: | CTCTTTCGTTTTCGTAAATAGTCTTCTTCATACATGGTCTAATAA | (45 mer) |
| L5: | TGTCAGAAGCGTAAACATACAATTGGTATTCGTACCCCTTAATTT | (45 mer) |
| L6: | TACCGCGGGTCTTGTAGTCTTCAGAAATGTCAGCTCTGAAAAGCT | (45 mer) |
| L7: | TCGACTATTATGGTGGTGGAACTGGACCGTTGAATCTCAACAACTTTC | (48 mer) |

The oligomers were isolated by urea-polyacrylamide gel electrophoresis and purified by passing through a Sep-pak C18 column (Whatman) and annealed and ligated as shown:

| NdeI | | | | | | SalI |
|---|---|---|---|---|---|---|
| U1 | U2 | U3 | U4 | U5 | U6 | U7 |
| L1 | L2 | L3 | L4 | L5 | L6 | L7 | to obtain the synthetic gene of FIG. 3 bracketed by NdeI and SalI sites.

For the ligation, each oligomer was phosphorylated at 37° C. for 45 minutes in a reaction mixture of 30 ul containing 50 mM Tris-HCl, pH 8.0, 10 mM $MgCl_2$, 10 mM DTT, 1 mMATP, and 5 units of T4 polynucleotide kinase. Each reaction mixture was pooled, extracted by phenol/chloroform, precipitated with ethanol, and dried under Speed-Vac. The dried pellet was dissolved in 50 ul distilled water and 7 ul ligation buffer (0.2M Tris-HCl, pH 7.5, 0.1M $MgCl_2$, 0.1M DTT) added. The solution was placed in a 95° C.

and incubated at 4° C. overnight to provide M13mp19 MON-1RF. The ligation mixture was transformed into hosts by adding 5 ul of the ligation mixture to 200 ul of E. coli JM101 competent cells (Messing, J., Methods in Enzymology (1983) 101:20–78), and the desired sequence was confirmed by dideoxy sequencing (Sanger, T., et al., Proc Natl Acad Sci USA (1985) 74:5463–5467).

Example 2

Preparation of An Expression Vector

The 293 bp NdeI/SalI synthetic gene was isolated from M13mp19 MON-1 RF and purified. A commercially available vector, pDR720, containing the trp promoter/operator (Pharmacia, Inc.; Cat. #27-4930-01) was digested with SmaI/PvuII and blunt-end ligated to produce ptrp322. The ptrp322 was digested with HpaI/SalI and a 2.5 kb large fragment isolated. A synthetic HpaI/NdeI adaptor,

| | |
|---|---|
| 5' - AACTAGTACGCAAGTTCACGTAAAAAGGGTAATACA - 3' | (36 mer) |
| 3' - TTGATCATGCGTTCAAGTGCATTTTTCCCATTATGTAT - 5' | (38 mer) |
| HpaI | NdeI | was synthesized using Applied Biosystems DNA Synthesizer Model 380B. The ligation reaction of the 293 bp synthetic monellin gene, HpaI/SalI-treated ptrp322 vector and the HpaI/NdeI synthetic adaptor was carried out in the presence of 10 ul of 20 mM Tris-HCl, pH 7.5, 10 mM $MgCl_2$, 10 mM DTT, and 200 units of T4 DNA ligase (New England Biolabs, Inc.) at 14° C. overnight to give ptrp322H MON-1. The ligation mixture was transformed into E. coli W3110 (ATCC 27325) and ampicillin-resistant clones were picked.

Example 3

Production of B-C-A

An overnight culture of 50 ul of ptrp322H MON-1 in W3110 with Luria Broth was inoculated into 5 ml of M9 media containing 0.4% casamino acid, 10 ug/ml vitamin B1, 40 ug/ml ampicillin and cultured at 37° C. in a temperature controlled-shaking incubator until $OD_{650nm}$ reached about 0.5. Then 0.1 mg of indolyl acrylic acid was added to the reaction mixture to a concentration of 50 ug/ml and the mixture incubated further for about 8 hours. The cultured cells were pelleted at 2500 rpm for 5 minutes in a Beckman J6 centrifuge. Laemmli protein sample buffer was added to the cell pellet, followed by heating at 95° C. for 5 minutes and the protein was loaded onto 15% Laemmli SDS polyacrylamide gel (Laemmli, *Nature* (1970) 227:680–685). The electrophoresis was run at 300 for 2.5 hours. The gel was stained with Coomassie blue brilliant dye demonstrating a product having the correct molecular weight. The expressed product was isolated and shown to have a sweet taste.

The product was dissolved in water and heated to 100° C. for 5 minutes. The solution was cooled to room temperature and the solution retasted. The sweet taste remained after the heating and cooling cycle.

Example 4

Purification of B-C-A

The cultured cells were sonicated in a buffer containing 0.01M sodium phosphate, pH 7.2, 7 mM betamercaptoethanol, 1 mM EDTA, 25 ug/ml PMSF protease inhibitor. The sample was spun at 10,000 rpm for 15 min in a Sorvall SS34 rotor at 4° C. The extract was diluted with the buffer. The sample was loaded on CM-25 Sephadex column preequilibrated with 0.01M phosphate buffer at pH 7.2. The column was washed with the same buffer for 3 hours. The product single chain monellin analog was eluted with 0.01M phosphate buffer plus 0.1M NaCl. After dialysis against water, the purity of the protein was determined by gel electrophoresis. If necessary, the protein was further purified by affinity column of Sepharose CI-4B charged with polyclonal monellin antibodies.

Example 5

Preparation of Alternate B-C-As

Following the above procedures, modified DNA sequences were prepared having different "C" linking sequences (between nucleotides 141 and 166 of FIG. 3) as follows.

Tyr-Glu-Asn-Arg-Glu-Asp-Ile-Lys
Tyr-Ala-Ser-Asp-Lys;
Glu-Asp-Tyr-Lys-Thr-Arg;
Tyr-Glu-Asn-Arg-Glu-Asp-Ile-Lys;
Tyr-Lys-Thr-Arg-Glu-Asp-Ile-Lys;
Tyr-Glu-Arg-Glu-Ile-Lys;
Tyr-Glu-Asn-Ile-Lys;
Tyr-Glu-Ile-Lys;
Tyr-Tyr-Ala-Ser-Asp-Lys-Leu-Lys;
Tyr-Ala-Ser-Asp-Lys-Leu;
Tyr-Ser-Asp-Lys;
Glu-Asp-Tyr-Lys-Thr-Arg-Gly-Arg; and
Glu-Asp-Tyr-Thr-Arg.

The codons employed are the same as the codons indicated for the construct shown in FIG. 3.

Example 6

Test for Sweetness

Sweetness of the product was assessed using an ordinary taste test. Comparison to the sweetness of sucrose was made by suitable dilutions on a weight basis. Compounds of the invention have at least the same sweetness as sucrose when diluted about 1000-fold in comparison.

In a typical test, 1, 10, 25 and 50 mg/ml aqueous sugar solution were used as standard solutions. The minimum weight of test compound which can be added to the water in order for it still to taste sweet to the tester is compared with the corresponding minimum weight of sucrose. The compounds of the invention require the addition of only an amount of material which is about 100-fold less than sucrose, for example, 60 ug/ml protein solution was as sweet as 50 mg/ml sugar (Lucky Supermarket's Lady Lee brand sugar).

Stability under different pH conditions was measured by dissolving natural monellin (Worthington) and the product of Example 4 at 100 ug/ml concentration at pH 2, 4 and 6.3. Each sample was heated to 40, 50, 60, 70, 80, 90 and 100° C. for 15 min, then let cool to room temperature before tasting. The most dramatic difference was that natural monellin lost its sweetness when heated to 50° C. at pH 2 then let cool to room temperature for a taste test, while the product regained sweetness even after heating at 100° C. for 5 minutes.

We claim:

1. A DNA molecule in isolated and purified form which encodes a protein useful as a sweetener of the formula B-C-A, wherein B represents an amino acid sequence having at least 90% homology to the amino acid sequence at positions 1–46 of the B chain of native monellin as shown in FIG. 1 wherein corresponding nonidentical positions contain conservative substitutions;

C represents an amino acid sequence selected from the group consisting of

Tyr-Glu-Asn-Glu-Arg-Glu-Ile-Lys;
Tyr-Ala-Ser-Asp-Lys;
Glu-Asp-Asn-Arg-Glu-Asp-Ile-Lys;
Tyr-Lys-Thr-Arg-Glu-Asp-Ile-Lys;
Tyr-Glu-Arg-Glu-Ile-Lys;
Tyr-Glu-Asn-Ile-Lys;
Tyr-Glu-Ile-Lys;
Tyr-Tyr-Ala-Ser-Asp-Lys-Leu-Lys;
Tyr-Ala-Ser-Asp-Lys-Leu';
Tyr-Ser-Asp-Lys;
Glu-Asp-Tyr-Lys-Thr-Arg-Gly-Arg; and
Glu-Asp-Tyr-Thr-Arg, and A represents an amino acid sequence having at least 90% homology to the amino acid sequence at positions 6–45 of the A chain of native monellin as shown in FIG. 1 wherein corresponding nonidentical positions contain conservative substitutions.

2. An expression system effective, when contained in a host cell to produce a protein useful as a sweetener of the formula B-C-A, wherein B represents an amino acid sequence having at least 90% homology to the amino acid sequence at positions 1–46 of the B chain of native monellin as shown in FIG. 1 wherein corresponding nonidentical positions contain conservative substitutions;

C represents an amino acid sequence selected from the group consisting of

Tyr-Glu-Asn-Glu-Arg-Glu-Ile-Lys;
Tyr-Ala-Ser-Asp-Lys;
Glu-Asp-Asn-Arg-Glu-Asp-Ile-Lys;
Tyr-Lys-Thr-Arg-Glu-Asp-Ile-Lys;
Tyr-Glu-Arg-Glu-Ile-Lys;
Tyr-Glu-Asn-Ile-Lys;
Tyr-Glu-Ile-Lys;
Tyr-Tyr-Ala-Ser-Asp-Lys-Leu-Lys;
Tyr-Ala-Ser-Asp-Lys-Leu';
Tyr-Ser-Asp-Lys;
Glu-Asp-Tyr-Lys-Thr-Arg-Gly-Arg; and
Glu-Asp-Tyr-Thr-Arg, and A represents an amino acid sequence having at least 90% homology to the amino acid sequence at positions 6–45 of the A chain of native monellin as shown in FIG. 1 wherein corresponding nonidentical positions contain conservative substitutions which expression system comprises an oligonucleotide sequence encoding said protein operably linked to control sequences compatible with the host cell.

3. A recombinant host cell modified to contain the expression system of claim 2.

4. A method to produce a protein useful as a sweetener of the formula B-C-A, wherein B represents an amino acid sequence having at least 90% homology to the amino acid sequence at positions 1–46 of the B chain of native monellin as shown in FIG. 1 wherein corresponding nonidentical positions contain conservatative substitutions;

C represents an amino acid sequence selected from the group consisting of

Tyr-Glu-Asn-Glu-Arg-Glu-Ile-Lys;
Tyr-Ala-Ser-Asp-Lys;
Glu-Asp-Asn-Arg-Glu-Asp-Ile-Lys;
Tyr-Lys-Thr-Arg-Glu-Asp-Ile-Lys;
Tyr-Glu-Arg-Glu-Ile-Lys;
Tyr-Glu-Asn-Ile-Lys;
Tyr-Glu-Ile-Lys;
Tyr-Tyr-Ala-Ser-Asp-Lys-Leu-Lys;
Tyr-Ala-Ser-Asp-Lys-Leu';
Tyr-Ser-Asp-Lys;
Glu-Asp-Tyr-Lys-Thr-Arg-Gly-Arg; and
Glu-Asp-Tyr-Thr-Arg, and A represents an amino acid sequence having at least 90% homology to the amino acid sequence at positions 6–45 of the A chain of native monellin as shown in FIG. 1 wherein corresponding nonidentical positions contain conservative substitutions;

which method comprises culturing the cells of claim 3 under conditions wherein expression is effected to produce the protein; and recovering the protein from the culture.

5. The DNA molecule of claim 1 wherein C represents the amino acid sequence Tyr-Glu-Asn-Glu-Arg-Glu-Ile-Lys.

6. The expression system of claim 2 wherein C represents the amino acid sequence Tyr-Glu-Asn-Glu-Arg-Glu-Ile-Lys.

7. The recombinant host cell of claim 3 wherein represents the amino acid sequence Tyr-Glu-Asn-Glu-Arg-Glu-Ile-Lys.

8. The method of claim 4 wherein C represents the amino acid sequence Tyr-Glu-Asn-Glu-Arg-Glu-Ile-Lys.

9. The DNA molecule of claim 5 wherein B represents

|     |     | Gly | Glu | Trp | Glu | Ile | Ile | Asp | Ile | Gly |
|-----|-----|-----|-----|-----|-----|-----|-----|-----|-----|-----|
| Pro | Phe | Thr | Gln | Asn | Leu | Gly | Lys | Phe | Ala |
| Val | Asp | Glu | Glu | Asn | Lys | Ile | Gly | Gln | Tyr |
| Gly | Arg | Leu | Thr | Phe | Asn | Lys | Val | Ile | Arg |
| Pro | Cys | Met | Lys | Lys | Thr | Ile | and wherein A represents

|     |     |     |     |     | Gly | Tyr | Glu | Tyr | Gln |
|-----|-----|-----|-----|-----|-----|-----|-----|-----|-----|
| Leu | Tyr | Val | Tyr | Ala | Ser | Asp | Lys | Leu | Phe |
| Arg | Ala | Asp | Ile | Ser | Glu | Asp | Tyr | Lys | Thr |
| Arg | Gly | Arg | Lys | Leu | Leu | Arg | Phe | Asn | Gly |
| Pro | Val | Pro | Pro | Pro. |

10. The expression system of claim 6 wherein B represents

|     |     | Gly | Glu | Trp | Glu | Ile | Ile | Asp | Ile | Gly |
|-----|-----|-----|-----|-----|-----|-----|-----|-----|-----|-----|
| Pro | Phe | Thr | Gln | Asn | Leu | Gly | Lys | Phe | Ala |
| Val | Asp | Glu | Glu | Asn | Lys | Ile | Gly | Gln | Tyr |
| Gly | Arg | Leu | Thr | Phe | Asn | Lys | Val | Ile | Arg |
| Pro | Cys | Met | Lys | Lys | Thr | Ile | and wherein A represents

|     |     |     |     |     | Gly | Tyr | Glu | Tyr | Gln |
|-----|-----|-----|-----|-----|-----|-----|-----|-----|-----|
| Leu | Tyr | Val | Tyr | Ala | Ser | Asp | Lys | Leu | Phe |
| Arg | Ala | Asp | Ile | Ser | Glu | Asp | Tyr | Lys | Thr |
| Arg | Gly | Arg | Lys | Leu | Leu | Arg | Phe | Asn | Gly |
| Pro | Val | Pro | Pro | Pro. |

11. The recombinant host cell of claim 7 wherein B represents

|     |     |     |     |     | Gly | Glu | Trp | Glu | Ile | Ile | Asp | Ile | Gly |
|-----|-----|-----|-----|-----|-----|-----|-----|-----|-----|-----|-----|-----|-----|
| Pro | Phe | Thr | Gln | Asn | Leu | Gly | Lys | Phe | Ala |
| Val | Asp | Glu | Glu | Asn | Lys | Ile | Gly | Gln | Tyr |
| Gly | Arg | Leu | Thr | Phe | Asn | Lys | Val | Ile | Arg |
| Pro | Cys | Met | Lys | Lys | Thr | Ile | and wherein A represents

|     |     |     |     |     | Gly | Tyr | Glu | Tyr | Gln |
|-----|-----|-----|-----|-----|-----|-----|-----|-----|-----|
| Leu | Tyr | Val | Tyr | Ala | Ser | Asp | Lys | Leu | Phe |
| Arg | Ala | Asp | Ile | Ser | Glu | Asp | Tyr | Lys | Thr |
| Arg | Gly | Arg | Lys | Leu | Leu | Arg | Phe | Asn | Gly |
| Pro | Val | Pro | Pro | Pro. |

12. The method of claim 8 wherein B represents

|     |     |     |     |     | Gly | Glu | Trp | Glu | Ile | Ile | Asp | Ile | Gly |
|-----|-----|-----|-----|-----|-----|-----|-----|-----|-----|-----|-----|-----|-----|
| Pro | Phe | Thr | Gln | Asn | Leu | Gly | Lys | Phe | Ala |
| Val | Asp | Glu | Glu | Asn | Lys | Ile | Gly | Gln | Tyr |
| Gly | Arg | Leu | Thr | Phe | Asn | Lys | Val | Ile | Arg |
| Pro | Cys | Met | Lys | Lys | Thr | Ile | and wherein A represents

|     |     |     |     |     | Gly | Tyr | Glu | Tyr | Gln |
|-----|-----|-----|-----|-----|-----|-----|-----|-----|-----|
| Leu | Tyr | Val | Tyr | Ala | Ser | Asp | Lys | Leu | Phe |
| Arg | Ala | Asp | Ile | Ser | Glu | Asp | Tyr | Lys | Thr |
| Arg | Gly | Arg | Lys | Leu | Leu | Arg | Phe | Asn | Gly |
| Pro | Val | Pro | Pro | Pro. |

\* \* \* \* \*